United States Patent [19]

Eder et al.

[11] 4,032,540
[45] June 28, 1977

[54] BENZOPYRAN DERIVATIVES

[75] Inventors: Ulrich Eder; Gerhard Sauer; Gregor Haffer; Jürgen Ruppert; Rudolf Wiechert, all of Berlin, Germany

[73] Assignee: Schering Aktiengesellschaft, Berlin & Bergkamen, Germany

[22] Filed: Mar. 5, 1976

[21] Appl. No.: 664,316

Related U.S. Application Data

[62] Division of Ser. No. 367,509, June 6, 1973, Pat. No. 3,962,280.

[30] Foreign Application Priority Data

June 8, 1972  Germany ............................ 2228473
June 8, 1972  Germany ............................ 2228475

[52] U.S. Cl. .......................................... 260/340.5
[51] Int. Cl.² ..................................... C07D 317/44
[58] Field of Search ............ 260/340.5 AS, 340.5 R

[56] References Cited

UNITED STATES PATENTS 3,655,695  4/1972  Andrews et al. ............... 260/340.5

*Primary Examiner*—Ethel G. Love
*Attorney, Agent, or Firm*—Millen & White

[57] ABSTRACT

Benzopyran derivatives of the formula

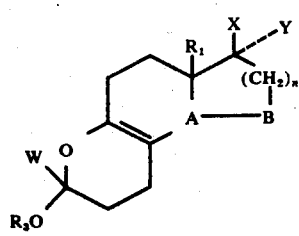

wherein $R_1$ and $R_3$ each are lower alkyl; $n$ is the integer 1 or 2; —A—B— is >CH—$CH_2$- or >CH=CH-; X is a free, esterified or etherified hydroxy group; and Y is H or X and Y collectively are =O; and W is —($CH_2$)$_3$—Z—$R_4$

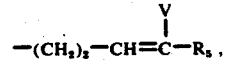

—($CH_2$)$_3$—$COOR_4$ or —($CH_2$)$_3$CN, wherein V is halogen, Z is a ketalized carbonyl group or a free, esterified or etherified hydroxymethylene group; $R_4$ and $R_5$ each are lower alkyl and $R_4$ is alkyl, aryl or aralkyl, are valuable intermediates in the synthesis of steroids.

14 Claims, No Drawings

BENZOPYRAN DERIVATIVES

This is a division of application Ser. No. 367,509 now U.S. Pat. No. 3962280, filed June 6, 1973.

BACKGROUND OF THE INVENTION

This invention relates to novel benzopyran derivatives.

In copending, commonly assigned U.S. Application Ser. No. 261,216, file June 9, 1972 now U.S. Pat. No. 3,849,447, are described benzopyran derivatives of the general Formula I

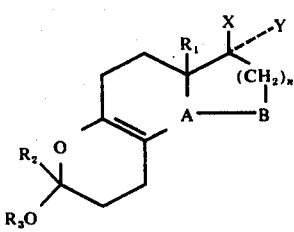

wherein $R_1$, $R_2$ and $R_3$ are each lower alkyl; $n$ is 1 or 2; >A-B- is >CH-CH$_2$- or >C=CH-; X is free, esterified or etherified hydroxy; Y is H or X and Y collectively are =O.

Also disclosed therein is a process for the preparation of these benzopyran derivatives in which a compound of the general Formula II

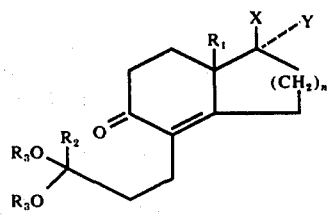

wherein $R_1$, $R_2$, $R_3$, X, Y and $n$ have the values given for Formula I, is cyclized in the presence of an acidic catalyst; and, optionally when X and Y are a keto group, the group is reduced to a hydroxy group; when a double bond is present in —A-B, the group is hydrogenated; when X is a free hydroxy group, the group is esterified or etherified and when X is an esterified hydroxy group, the group is hydrolyzed.

One drawback of the useful compounds described in the aforementioned copending application is the number of steps required to produce the starting materials therefor, which are described in more detail in the aforementioned U.S. Pat. No. 3,849,447. It is an object of the present invention to provide useful intermediates for the production of pharmacologically active steroids for which the starting materials are easily prepared.

Furthermore, the compounds of the aforementioned copending application are intermediates for the production of des-A-steroids and it is an object of the present invention to provide useful intermediates which can be converted to steroids. per se.

The present invention relates to novel benzopyran derivatives which differ from the compounds of the prior-filed application by the type of $R_2$ groups in the molecule.

SUMMARY OF THE INVENTION

Accordingly, this invention relates to novel benzopyran derivatives of the general Formula III

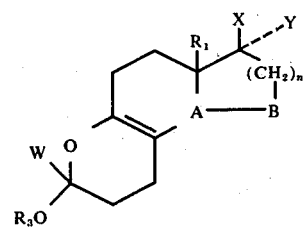

wherein $R_1$, $R_3$, n, X, Y and -A-B- have the above-indicated values and W is —(CH$_2$)$_3$-Z-R$_4$;

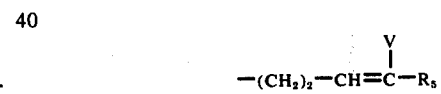

—(CH$_2$)$_3$COOR$_6$; or —(CH$_2$)$_3$CN, wherein V is a halogen atom, Z is ketalized carbonyl or free, esterfied or etherified hydroxymethylene, $R_4$ and $R_5$ are lower alkyl and $R_6$ is alkyl, aryl or aralkyl.

DETAILED DISCUSSION

Of the compounds of this invention preferred are those compounds of Formula III meeting one or more of the following definitions:
a. n is 1;
X is a free, esterified or etherified hydroxyl and Y is H, or X and Y collectively are =O;
c. one or both of $R_1$ and $R_3$ are methyl or ethyl;
d. W is -(CH$_2$)$_3$-Z-R$_4$ wherein Z is alkylene or arylene dioxymethylene, especially when $R_4$ is methyl or ethyl;
e. W is $$-(CH_2)_2-CH=C(V)-R_5$$

wherein V is chlorine or bromine, especially when $R_5$ is methyl or ethyl;
f. W is —(CH$_2$)$_3$-COOR$_6$ wherein $R_6$ is alkyl of 1-10 carbon atoms, phenyl or phenylalkyl of 1-4, preferably 1-2 carbon atoms in the alkyl group, e.g., benzyl or phenylethyl;
g. W is —(CH$_2$)$_3$CN.

Compounds of this invention, in addition to those shown in the following examples, include:

3-methoxy-7α-benzoyloxy-6aα-methyl-3-(3'-cyanopropyl)-1,2,3,5,6,7β,8,9,9aβ-decahydrocyclopenta-[f][1]-benzopyran, 3-ethoxy-7α-acetoxy-6aα-ethyl-3-(4'-bromo-3'-pentenyl)-1,2,3,5,6,6a,7β,8,9,9aβ-decahydrocyclopenta-[f][1]-benzopyran, 3-butyloxy-7α-methoxy-6aα-methyl-3-(4'-methoxypentyl)1,2,3,5,6,6a,7β, 8,9,9aβ-decahydrocyclopenta-[f][1]-benzopyran, 3-methoxy-7α-tert.-butyloxy-6aα-ethyl-3-(4'-acetoxypentyl)-1,2,3,5,6,6a,7β,8,9,9aβ-decahydrocyclopenta-[f][1]-benzopyran, and 3-ethoxy-7α-tert.-butyloxy-6aα-methyl-3-(4',4'-o-phenylendioxypentyl)-1,2,3,5,6,6a,7β,8,9,10-decahydrocyclohexa-[f][1]-benzopyran.

It will be apparent to those skilled in the art that when X is other than OH, the exact nature of the ester or ether group is not critical to the utility of the compounds of Formula III as intermediates in the production of the steroids and can thus be varied in a conventional manner without destroying their effectiveness. Thus, compounds of this invention include those wherein X is acyloxy, acyl being the acyl group or any organic acid, e.g., a craboxylic-acid containing up to 18 carbon atoms, especially lower (1–6) carbon atoms and intermidate (7–12) aliphatic carboxylic, preferably an alkanoic acid, which can be unsaturated, branched, polybasic or substituted in the usual manner, for example by hydroxy or halogen atoms; a cycloaliphatic, aromatic and mixed aromatic-aliphatic (alkaryl and aralkyl) acid, which can likewise be substituted in the usual manner, e.g., acids containing 1–18, preferably 2–12 carbon atoms, including an aliphatic acid containing 1–18, preferably 1–6 carbon atoms, e.g., formic, acetic, propionic, butyric, isobutyric, α-ethylbutyric, caproic, valeric, isovaleric, α-ethylvaleric, 2-methylbutyric, 3-ethylbutyric, hexanoic, trimethylacetic, diethylacetic, triethylacetic, enanthic, actanoic, undecyclic, oleic and palmitic acid; a cyclic acid, preferably a cycloaliphatic acid, containing, e.g., 5–18 carbon atoms, e.g., cyclopropylideneacetic, cyclobutylcarboxylic, cyclopentylcarboxylic, cyclopentylacetic, cyclopenylpropionic, cyclohexylcarboxylic, cyclohexylacetic and β-cyclohexylpropionic acid, phenylpropionic acid, phenylacetic acid; a carbocyclic aryl or alkaryl acid, e.g., containing 6–18 carbon atoms, and 1 to 5, preferably 1 or 2 rings, e.g., benzoic, 2-, 3-, or 4-methyl-benzoic, 2,3-, 2,4-, 2,5-, 2,6-, 3,4- and 3,5-dimethylbenzoic, ethylbenzoic, 2,3,6-trimethylbenzoic and 3-methyl-α-naphthoic acid; an aralkyl acid, e.g., containing 7 to 18 carbon atoms, e.g., β-phenylpropionic, a polybasic acid, e.g., containing 2–18 carbon atoms and 0 to 5 hydroxy groups, e.g., glycolic, succinic, latic, citric, tartaric, d-maleic, d-glyceric and salicyclic acid; the corresponding acids containing one, two or more simple substituents, e.g., halo, alkoxy, acyloxy, etc., in the molecule, e.g., chloroacetic, fluoroacetic, dichloroacetic, trichloroacetic, trifluoroacetic, 2,3,4-trimethoxybenzoic, phenoxyacetic, α-naphthoxyacetic acid, etc.

The ester group can also be an ester of a sulfonic acid, e.g.; an arylsulfonic, including benzenesulfonic, p-toulenesulfonic, m,m'-dimethylbenzenesulfonic, o,o'-dimethylbenzenesulfonic, sym.-trimethylbenzenesulfonic, sym-triethylbenzenesulfonic, m-ethylbenzenesulfonic, para-isopropylbenzenesulfonic, m-n-butylbenzenesulfonic acid, or an alkylsulfonic, e.g., methanesulfonic, ethanesulfonic, propanesulfonic, isopropanesulfonic, butanesulfonic, tert.-butanesulfonic, pentanesulfonic, isopentanesulfonic, hexanesulfonic, heptanesulfonic, octylsulfonic or heterocycliocsulfonic, e.g., α-pyridinesulfonic, α-pyranesulfonic, α-thiophensulfonic, %-furansulfonic, %-tetrahydrofuransulfonic, or other alkyl-, carbocyclic and heterocyclic aryl-, alkaryl- and aralkyl-sulfonic acid, preferably one containing 1–8 carbon atoms and 0–2, preferably 0–1 N, S or O heteroatoms, which are preferably ring carbon atoms in a heterocyclic ring.

The $R_1$, $R_3$, $R_4$ and $R_5$ lower alkyl groups are preferably those of 1–4 carbon atoms. Examples of such alkyl groups include but are not limited to methyl, ethyl n-propyl, isopropyl and/or n-butyl. Especially preferred $R_1$, $R_3$, $R_4$ and $R_5$ groups are methyl and ethyl.

Preferred alkyl, aryl or aralkyl groups $R_6$ are those of 1–10 carbon atoms. Suitable residues $R_6$ include but are not limited to methyl, ethyl, n-propyl, isopropyl, n-butyl, tert. butyl, pentyl, hexyl, phenyl, benzyl or phenylethyl.

Preferred esterified and etherified hydroxyl X groups are acyloxy wherein acyl is the acyl radical of a hydrocarbon carboxylic acid of 1–10 carbon atoms and alkoxy of 1–10 carbon atoms which optionally can be substituted by phenyl. Specific examples include but are not limited to acetoxy, propionyloxy, butyryloxy, trimethylacetoxy, pentanoyloxy, hexanoyloxy, heptanoyloxy, octanoyloxy and benzoyloxy. Examples for alkoxy which optionally can be phenyl-substituted include but are not limited to methoxy, ethoxy, propoxy, isopropoxy, butoxy, tert. butoxy and benzoxy.

The group Z can be a ketalized carbonyl group or a free, esterified or etherified hydroxymethylene group. Suitable ketalized carbonyl groups Z are alkylene or arylene dioxymethylene, e.g., 1,2-ethylenedioxymethylene; 1,3-propylenedioxymethylene; 2,3-butylenedioxymethylene; 2',2'-dimethyl 1',3'-propylenedioxymethylene; 2,4-pentylenedioxymethylene group; or 1,2-phenylenedioxymethylene.

As esterified hydroxymethylene groups Z, those groups can be employed preferably, the acyl residues of which have 1–10 carbon atoms as defined hereinabove for esterified hydroxyl X groups. Suitable acyl residues include but are not limited to propionyloxy, butyryloxy, trimethylacetoxy, pentanoyloxy, hexanoyloxy, heptanoyloxy, octanoyloxy or benzoyloxy.

Suitable etherified hydroxymethylene groups Z are preferably alkoxymethylene groups or aralkoxymethylene groups of 1–10 carbon atoms in the alkoxy or aralkoxy residue. Suitable alkoxy or aralkoxy residues include but are not limited to methoxy, ethoxy, propyloxy, butyloxy, tert.-butyloxy, isopropyloxy or benzyloxy.

Preferred halogen atoms V are chlorine or bromine atoms.

In its process aspect, this invention relates to a process for the preparation of the novel benzopyran derivatives of Formula II by cyclizing a compound of the general Formula IV

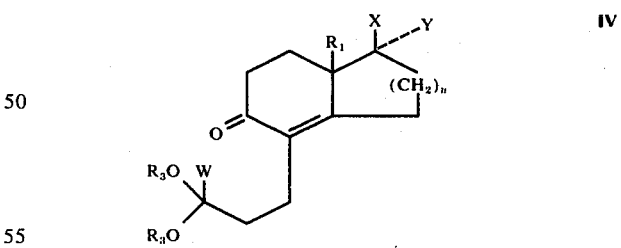

wherein $R_1$, $R_3$, W, X, Y and n have the values given above for Formula III, in the presence of acidic catalysts; and optionally thereafter conducting one or more of the following steps: reducing a keto group when X = O; hydrogenating a double bond present in —A—B—; and/or esterifying or etherifying a free hydroxy group when X = OH; and hydrolyzing an ester group or cleaving an ether group when X is an esterified or etherified hydroxy group.

The cyclization of the starting compounds of general Formula IV is effected under the influence of an acidic catalyst. Suitable catalysts for the cyclization are, in particular, carboxylic acids and phenols, e.g., formic acid, acetic acid, propionic acid, monofluoroacetic acid, trichloroacetic acid, methoxyacetic acid, trimethylacetic acid, cyclopentylpropionic acid, benzoic acid, p-hydroxybenzoic acid, p-nitrobenzoic acid, phenoxyacetic acid, phenylacetic acid, oxalic acid, malonic acid, succinic acid, phenol, o-, m-, or p-cresol, o-, m- or p-chlorophenol, resorcinol, p-nitrophenyol, 2,4-dinitrophenol and 2,4,6-trinitrophenol.

On other other hand, it is also possible to employ as the acidic catalyst for the cyclization mineral acids, sulfonic acids, or Lewis acids, e.g., hydrogen chloride, sulfuric acid, phosphoric acid, perchloric acid, methanesulfonic acid, benzenesulfonic acid, p-toluenesulfonic acid and boron trifluoride.

The acids or phenols utilized for the cyclization are preferably employed in catalytic amounts, for example, 0.1 mol to 0.001 mol of acidic catalyst per mole of starting compound.

The cyclization is preferably conducted in an aprotic solvent. Suitable solvents include but are not limited to ethers, e.g., diethyl ether, diisopropyl ether, di-n-butyl ether, tetrahydrofuran, anisole and dimethoxyethane; hydrocarbons, e.g., hexane, cyclohexane, benzene, toluene and xylene; and chlorinated hydrocarbons, e.g., carbon tetrachloride, chloroform, tetrachloroethane, 1,2-dichloroethane and chlorobenzene. Alcohols, e.g., methanol, ethanol, n-propanol and n-butanol can also be employed as solvents for the cyclization When conducting the cyclization reaction, it is advantageous to remove the alcohol used as the solvent or liberated during the cyclization by distillation or vacuum distillation from the reaction mixture.

The cyclization can be effected at a low temperature as well as at an elevated temperature, preferably 0° C. to 150° C.

It is surprising that the compounds of Formula IV are cyclized in the presence of an acidic catalyst to compounds of Formula III wherein —A—B— is >C=CH-.

The nonconjugated keto group (X = O) present in the cyclization products can, if desired, be reduced to an hydroxyl group in a conventional manner. This reduction can be conducted, for example, with complex metal hydrides, e.g., sodium borohydride, lithium aluminum hydride, lithiam tri-tert.-butoxy aluminum hydride or diisobutyl aluminum hydride. The method of Meerwein-Ponndorf can also be utilized for the reduction, for example, by reacting a ketone of Formula IV (X = O) with a secondary alcohol, e.g., isopropanol, in the presence of an aluminum alcoholate, e.g., aluminum isopropylate. These reducing agents are suitable especially for the preparation of compounds of Formula III wherein the thus-formed hydroxyl group is in the α-position.

The compounds of Formula III wherein —A—B— is >C=CH- can optionally be hydrogenated to analogous compounds wherein —A—B—is >CH-CH₂-. This hydrogenation is preferably effected with catalytically activated hydrogen, suitable catalysts being primarily heavy metal and/or noble metal hydrogenation catalysts, e.g.. Raney nickel, palladium, rhodium and platinum oxide catalysts. In these hydrogenation processes, those compounds are preferably formed wherein the hydrogen atom entering at the tertiary carbon atom is oriented in a β-configuration.

A free hydroxyl group X can optionally be esterified or etherified by method known per se in the art. For example, esterification of the free hydroxyl group of the hydroxyl compounds of the general Formula III can be conducted with carboxylic acid anhydrides or carboxylic acid chlorides in the presence of a base, e.g., sodium bicarbonate, potassium bicarbonate, pyridine or collidine.

To etherify the free hydroxyl group (X = OH), a conventional Williamson etherification method can be employed, for example.

The benzopyran derivatives of Formula III produced according to the process of this invention are valuable intermediates. They are especially suitable for producing pharmacologically effective steroids by total synthesis.

Thus, for example, the 6aβ-alkyl-3-alkoxy-2,3,5,6,6a,8,9,9aβ-octahydrocyclopenta-[f][1]-benzopyran-7[1H]-α-ols substituted in the 3-position, as produced according to the process of this invention, can be converted into the corresponding des-A-17β-hydroxy-13-alkyl-9-gonen-5-ones substituted in the 10-position by heating with hydrochloric acid in dioxane. The 17-esters and ethers of these benzopyranols can be hydrolyzed at the 17-position in a conventional manner after the cyclization has been accomplished.

The thus-prepared des-A-17β-hydroxy-13-alkyl-9-gonen-5-ones substituted in the 10-position can be converted in a conventional manner into pharmacologically valuable steroids, e.g., ostrone, ostradiol, 18-mothylestradiol, oquilenin, testosterone, 18-methyltestosterone, 17β-ethinyl-19-nortestosterone, or 17α-ethinyl-18-methyl-19-nortestosterone and the corresponding 18-homologues thereof. By reacting the compounds of Formula II wherein n is 2 in the same manner, the corresponding D-homosteroids are obtained.

Illustrative techniques for preparing pharmacologically active steroids are described in the literature, e.g., Helv.Chim. Acta. 54: 2857(1971) and 55: 1333(1972); U.S. Pat. No. 3,491,131; J.Amer.Chem.-Soc.,89. 5464(1967).

The starting compounds of the process of this invention can be synthesized, for example, in the following manner:

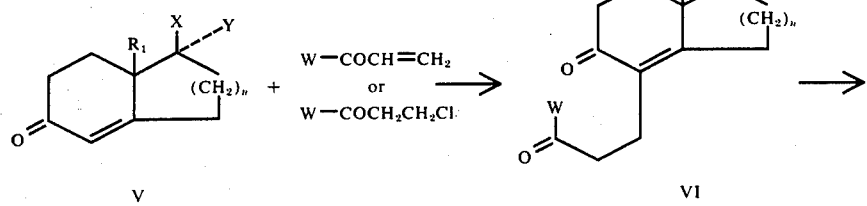

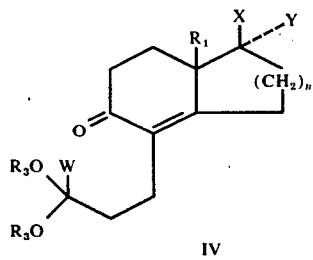

In the above formulae, $R_1$, $R_3$, W, X, Y and n have the above-indicated values.

The compounds of Formula IV can be produced, for example, under the following reaction conditions:

A compound of Formula V is dissolved in absolute tetrahydrofuran; 0.2 molar equivalents of sodium hydride is added thereto, and the mixture is heated under reflux until the formation of hydrogen is terminated. Then, the mixture is cooled to 10° – 30° C., admixed with a vinyl ketone of the formula $WCOCH=CH_2$ and agitated for 24–48 hours and worked up in the usual manner to yield a compound of Formula VI.

Another procedure for preparing the compounds of Formula VI is the following, for example:

A compound of Formula V is dissolved in absolute dimethoxyethane; 1.2 molar equivalents of sodium hydride is added thereto, and the mixture is heated under reflux until the evolution of hydrogen is terminated. Then, the mixture is cooled to −20° C. to −50° C., mixed with a β-chloroketone of the formula $WCOCH_2CH_2Cl$, agitated for 1–5 hours at a low temperature (−20° C. to −50° C.), and worked up as usual, e.g., by solvent extraction and purification using silica gel chromatography and/or recrysallization.

Compounds of Formula VI can be ketalized to compounds of Formula III with lower alcohols, preferably by reaction with a lower alkanol in the presence of an acidic catalyst, e.g., mineral acids, including hydrochloric acid, sulfuric acid and perchloric acid; sulfonic acids, e.g., methanesulfonic acid, benzenesulfonic acid, and p-toluenesulfonic acid; Lewis acids, e.g., boron trifluoride; and phenols, e.g., p-nitrophenol and 2,4-dinitrophenol.

The ketalizationis particularly successful if a waterbindinng agent is also present in the reaction mixture. Suitable water-binding agents are, for example, anhydrous sodium sulfate, anhydrous magnesium sulfate and anhydrous calcium sulfate. Also suitable as waterbinding agents are the orthoformic acid esters of the alcohols utilized for the ketalization.

The ketalization is preferably conducted at a reaction temperature of from −20° C. to +80° C. The ketalization can be conducted, for example, as follows:

Mix one mol of a compound of Formula VI with 2.5 mols of an orthoformic acid ester $(R_3O)_3CH$ and about 8–10 mols of an alcohol $R_3OH$. Then, add 3 ml. of a 0.5% alcoholic p-toluenesulfonic acid solution to the mixture and allow the reaction mixture to stand for about 30–180 minutes at room temperature.

The reaction mixture containing the compound of Formula IV obtained by the ketalization of a compound of Formula VI basically can be employed without any further purification for conducting the cyclization step of the process of this invention. This is possible because the compounds of Formula IV are cyclized, under the present reaction conditions, to compounds of Formula III wherein —A—B— is >C=CH-, when the reaction temperature is elevated or when the reaction time is lengthened. In this connection, it is advantageous to remove the alcohol utilized as the solvent by vacuum distillation and optionally to replace the alcohol by an aprotic solvent, e.g., benzene or toluene.

It is also possible to isolate the compounds of Formula IV as pure products. For this purpose, the reaction mixture is poured into ice-cold bicarbonate solution after the termination of the ketalizaton reaction, extracted with ether, the ether phase concentrated under vacuum, and the residue purified by chromatography and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1 a. 162 g. of 5-oxohexanonitrile is dissolved in 1 l. of toluene, 243 g. of pyrocatechol and 3 g. of p-toluenesulfonic acid are added thereto, and the mixture is heated for 24 hours on a water trap.

The reaction mixture is allowed to cool, then diluted with 1 l. of benzene, and the organic phase is washed with 1N sodium hydroxide solution and dilute sodium chloride solution, dried over sodium sulfate, and concentrated under vacuum. The thus-obtained crude product is distilled under a high vacuum, resulting in 246.5 g. of 5,5-o-phenylenedioxyhexanonitrile.

B.p.$_{0.1\ torr}$ = 106°–110° C.

b. 183 g. of 5,5-o-phenylenedioxyhexanonitrile is dissolved in 1830 ml. of toluene; the solution is cooled to −50° C. and mixed, within 1 hour, with 790 ml. of a 20% solution of diisobutyl aluminum hydride in toluene. Thereafter, the reaction mixture is agitated for one hour at −50° C.

Then, the reaction mixture is acidified with 4N hydrochloric acid to a pH of 3, diluted with 1 l. of ethyl acetate, and the organic phase is washed with dilute sodium chloride solution, dried over sodium sulfate, and concentrated to dryness under vacuum. The residue is distilled under a high vacuum, thus obtaining 174 g. of 5,5-o-phenylenedioxyhexanal.

B.p.$_{0.05\ torr}$ = 90°–92° C.

(c). 40 g. of magnesium filings are reacted in 800 ml. of tetrahydrofuran with vinyl chloride; the thusobtained solution is cooled to −30° c., added dropwise to a solution of 173 g. of 5,5-o-phenylenedioxyhexanal in 1800 ml. of tetrahydrofuran, and the reaction mixture is stored for 3 hours at −30° C. Then, the mixture is mixed dropwise with 260 ml. of saturated ammonium chloride solution, filtered, and the thus-obtained solution is concentrated under vacuum.

The residue is dissolved in 2000 ml. of acetone, the solution is cooled to −10° C., and within 30 minutes mixed with 200 ml. of Jones reagent (an aqueous solution, containing 267 g. of chromium(VI) oxide and 230 ml. of concentrated sulfuric acid per liter).

the mixture is allowed to stand for one hour, mixed with 100 ml. of methanol and 7000 ml. of methylene chloride, the organic phse is separated, washed with dilute solution of sodium chloride, dried over sodium sulfate, and concentrated under vacuum. The thus-obtained crude product is distilled under the high vacuum, thus producing 172 g. of 7,7-o-phenylenedioxy-1-octen-3-one.

B.p.$_{0.002\ torr}$ = 88°–92° C.

d. 23 g. of 7,7-o-phenylenedioxy-1-octen-3-one is dissolved in 150 ml. of chloroform and cooled to about 0° C. Then, dry hydrogen chloride is passed through the solution for 30 minutes. the chloroform is distilled off under vacuum at a bath temperature of 20° C., and the product thus obtained is 23.9 g. of 1-chloro-7,7-o-phenylenedioxyoctan-3-one.

e. 17 g. of 1β-tert.-butoxy-7aβ-methyl-5, 6, 7, 7a-tetrahydroindan-5-one is dissolved in 200 ml. of absolute dimethoxyethane and refluxed after the addition of 2 g. of sodium hydride for 2 hours. Thereafter, the solution is cooled to −20° to −30° C. and, within one hour, a solution of 21.5 g. of 1-chloro-7,7-o-phenylenedioxyoctan-3-one in 80 ml. of absolute dimethoxyethane is added dropwise thereto. After this step, the reaction solution is allowed to reach room temperature during the course of 3 hours. After another 3 hours, 50 ml. of saturated primary sodium phosphate solution is added thereto and the mixture worked up.

The crude product is purified with the use of chromatography on silica gel by means of hexane-acetone gradients, thus obtaining 22.4 g. of 1β-tert.-butoxy-7aβ-methyl-4-(7′,7′-o-phenylenedioxy-3′-ketooctyl)-5,6,7,7a-tetrahydroindan-5-one as a colorless oil.

IR bands at 5.86 μ; 6.00 μ; 6.72 μ; and 8.1 μ. $[\alpha]_D^{20}$ = +46° (c = 1, benzene).

f. 10.3 g. of 1β-tert.-butoxy-7aβ-methyl-4-(7′,7′-o-phenylenedioxy-3′-ketooctyl)-5,6,7,7a-tetrahydroindan-5-one is dissolved in 100 ml. of absolute methanol and 10.3 ml. of trimethyl orthoformate. The, the reaction mixture is cooled to 0° C. and 1.5 ml. of 0.5% methanolic p-toluenesulfonic acid solution is added thereto, whereafter the mixture is stirred at 0° C. for 4 hours. Then, the reacton solution is poured on 500 ml. of ice-cold dilute sodium bicarbonate solution and extracted with methylene chloride; the solution is washed with half-saturated sodium chloride solution, dired with sodium sulfate, the solvent is distilled off, and the mixture is recrystallized from ether.

The product is 9.95 g. of 1β-tert.-butyloxy-7aβ-methyl-4-(3′,3′-dimethoxy-7′,7′-o-phenylenedioxyoctyl)-5,6,7,7a-tetrahydroindan-5-one, m.p. 132°–134° C.

$[\alpha]_D^{21}$ = +42.5° (c = 1, benzene).

g. 11.3 g. of 1β-tert.-butyloxy-7aβ-methyl-4-(3′,3′-dimethoxy-7′,7′-o-phenylenedioxyoctyl)-5,6,7,7a-tetrahydroindan-5-one is dissolved in 200 ml. of absolute benzene, and 100 mg. of malonic acid is added thereto. Then, the mixture is heated under reflux, withdrawing 100 ml. of distillate within one hour. The solution, after cooling, is then mixed with 100 ml. of saturated sodium bicarbonate solution and worked up as usual, thus obtaining 10.3 g. of 3-methoxy-7α-tert.-butyloxy-6aα-methyl-3-(4′,4′-o-phenylenedioxypentyl)-1,2,3,5,6,6a,7β,8-octahydrocyclopenta[f][1]-benzopyran as a colorless oil IR bands at 6.0 μ; 6.75 μ; and 8.1 μ. $[\alpha]_D^{21}$ = +1.8° c = 1.01, benzene).

h. 10.1 g. of 3-methoxy-7α-tert.-butyloxy-6aα-methyl-3-(4′,4′-o-phenylenedioxypentyl)-1,2,3,5,6,6a,7β,8-octahydrocyclopenta-[f][1]-benzopyran is dissolved in 150 ml. of ethyl acetate and hydrogenated, after the addition of 0.6 g. of palladium charcoal (10%), at room temperature and under normal pressure. The absorption of hydrogen is terminated after 2.5 hours. The catalyst is filtered off and the solvent removed under vacuum. The crude product is purified by chromatography on silica gel, thus obtaining 9.45 g. of 3-methoxy-7 α-tert.-butyloxy-6aα-methyl-3-(4′, 4′-o-phenylenedioxypentyl)-1,2,3,5,6,-6a,8,9,9a β-decahydrocyclopenta-[f][1]-benzopyran as a colorless oil.

IR bands at 6.76 μ and 8.1 μ.

$[\alpha]_D^{21}$ = +16.6° c = 1, benzene).

EXAMPLE 2

12 g. of racemic 1β-tert.-butyloxy-7aβ-ethyl-5,6,7,7a-tetrahydroindan-5-one is dissolved in 150 ml. of absolute tetrahydrofuran, and 400 mg. of sodium hydride is added thereto. Under a protective argon gas atmosphere, the mixture is then refluxed until the evolution of hydrogen is terminated; then, the solution is cooled to 0° C. Under agitation, a solution of 13 g. of 7,7o-phenylenedioxy-1-octen-3-one in 50 ml. of absolute tetrahydrofuran is then added within 30 minutes, and the mixture is stirred for another 30 hours at 0° C. The crude product resulting from the usual working-up process is purified by chromatography on silica gel, thus obtaining 10.5 g. of 1β-tert.-butyloxy-7aβ-ethyl-4-(7′, 7′o-phenylenedioxy-3′-keto-octyl)-5,6,7,7a-trahydroindan-5-one as a colorless oil.

IR bands at 5.85 μ; 6.05 μ; 6.75 μ; and 8.1μ.

b. 3.8 g. of racemic 1β-tert.-butyloxy-7aβ-ethyl-4-(7′,7′-o-phenylenedioxy-3′-ketooctyl(-5,6,6,7,a-tetrahydroindan-5-one is reacted, as in Example 1(f), with methanol and trimethyl orthoformate at 0° C., worked up, and the product thus obtained is 3.81 g. of 1β-tert.-butyloxy-7aβ-ethyl-4-(3′,3′-dimethoxy-7′,7′-o-phenylenedioxyoctyl)-5,6,7,7a-tetrahydroindan-5-one as a colorless oil.

IR bands at 6.06 μ; 6.75 μ; and 8.1 μ.

c. 3.82 g. of racemic 1β-tert.-butyloxy-7aβ-ethyl-4-(3′,3′-dimethoxy-7′,7′-phenylenedioxyoctyl)-5,6,7,7a-tetrahydroindan-5-one is reacted according to Example 1(g), worked up and the product thus prepared is 3.34 g. of 3-methoxy-7α-tert.-butyloxy-6aα-ethyl-3-(4′, 4′-o-phenylenedioxypentyl)-1,2,3,5,6,6a,7β,8-octahydrocyclopenta-[f][1]-benzopyran as a colorless oil.

IR bands at 6.0 μ; 6.75 μ;and 8.1 μ.

d. 3.25 g. of 3-methoxy-7α-tert.-butyloxy-6aα-ethyl-3-(4′,4′-o-phenylenedioxypentyl)-1,2,3,5,6,6a,7β,8-octahydrocyclopenta-[f][1]-benzopyran is hydrogenated and worked up as set forth in Example 1(h), thus obtaining 2.91 g. of 3-methoxy-7α-tert.-butyloxy-6aα-ethyl-3-(4′,4′-o-phenylenedioxypentyl)-1,2,3,5,6,6a,7β-decahydrocyclopenta-[f][1]-benzopyran in the form of an oil.

IR bands at 6.75 μand 8.1 μ.

EXAMPLE 3 a. 15.8 g. off 7-chloro-1,6-octadien-3-one is dissolved in 150 ml. of absolute chloroform and cooled to 0° C. Then, dry hydrogen chloride is introduced into the mixture for 30 minutes, the solution is concentrated to dryness under vacuum, and the product thus prepared in 16.5 g. of 1,7-dichloro-6-octen-3-one as a colorless oil.

IR bands at 5.86 $\mu$ and 5.97 $\mu$.

b. 11 g. of racemic trimethylacetoxy-7a$\beta$-methyl-5,6,7,7a-tetrahydroindan-5-one is dissolved in 100 ml. of dimethylformamide and 50 ml. of benzene and, after the addition of 1.3 g. of sodium hydride, heated to 60–70° C. under an argon atmosphere.

The evolution of hydrogen is terminated after 3 hours. The mixture is then cooled to −10° C. and, within 45 minutes, a solution of 8.9 g. of 1,7-dichloro-6octen-3-one is added dropwise thereto. After the adding step, the mixture is further agitated for 15 hours at 0° C. Then, the procedure of Example 1(e) is followed, thus obtaining 9.7 g. of 1$\beta$-trimethylacetoxy-7a$\beta$-methyl-4-(7'-chloro-3'-keto-6'-octenyl)-5,6,7,7a-tetrahydroindan-5-one as a colorless oil.

IR bands at 5.85 $\mu$; 6.00 $\mu$; and 5.79 $\mu$.

c. 3.2 g. of racemic 1 $\beta$-trimethylacetoxy-7a$\beta$-methyl-4-(7'-chloro-3'-keto-6'-octenyl)-5,6,7,7a-tetrahydroindan-5-one is reacted as in Example 1(f) with 3.5 ml. of orthoformic acid ester and 30 ml. of absolute methanol under the catalysis of p-toluenesulfonic acid at 0° C., worked up, and the product thus obtained is 3.12 g. of 1$\beta$-trimethylacetoxy-7a$\beta$-methyl-4-(7'-chloro-3',3'-dimethoxy-6'-octenyl)-5,6,7,7a-tetrahydroindan-5-one as a colorless oil.

IR bands at 5.77 $\mu$ and 6.07 $\mu$.

d. 3.8 g. of 1$\beta$-trimethylacetoxy-7a$\beta$-methyl-4-(7'-chloro-3',3'-dimethoxy-6'-octenyl)-5,6,7,7a-tetrahydroindan-5-one is reacted according to Example 1(g) with p-nitrophenol in place of malonic acid and worked up, thus producing 3.35 g. of 3-methoxy-7$\alpha$-trimethylacetoxymethyl-3-(4'-chloro-3'-pentenyl)-1,2,3,5,6,6a,7$\beta$,8-octahydrocyclopenta-[f][1]-benzopyran as a colorless oil.

IR bands at 5.78 $\mu$, 6.0 $\mu$, and 6.1 $\mu$.

e. 2.3 g. of 3-methoxy-7$\alpha$-trimethylacetoxy-6a$\alpha$-methyl-3-(4'-chloro-3'-pentenyl)-1,2,3,5,6,6a,7$\beta$,8-octahydrocyclopenta-[f][1]-benzopyran is dissolved in 30 ml. of ethyl acetate and 3 ml. of triethylamine; after the addition of 300 mg. of rhodium charcoal (5%), the mixture is hydrogenated under normal pressure and at room temperature, the theoretical amount of hydrogen being absorbed within 5 hours. The crude product obtained after filtering off the catalyst and evaporation of the solvent is purified on a silica gel column, thus producing 1.2 g. of 3-methoxy-7$\alpha$-trimethylacetoxy-6a$\alpha$-methyl-3-(4'-chloro-3'-pentenyl)-1,2,3,5,6,6a,7$\beta$,8,9,9a$\beta$-decahydrocyclopenta-[f][1]-benzopyran as a colorless oil.

IR bands at 5.79 $\mu$ and 6.1 $\mu$.

EXAMPLE 4 a. 5.2 g. of racemic 1$\beta$-trimethylacetoxy-7a$\beta$-methyl-5,6,7,7a-tetrahydroindan-5-one is heated with 0.63 g. of sodium hydride in 50 ml. of dimethylformamide and 50 ml. of benzene until the evolution of hydrogen is terminated; this heating step is conducted at 60° C. Then, the reaction mixture is cooled to −10° C., and a solution of 4.3 g. of methyl 7-chloro-5-ketcheptanoate in 10 ml. of absolute benzene is added dropwise thereto within 20 minutes; then, the mixture is allowed to stand for 16 hours at 0° C. The crude product obtained after working the mixture up as usual is chromatographed on silica gel, thus obtaining 1$\beta$-trimethylacetoxy-7a$\beta$-methyl-4-(3'-keto-6'-methoxycarbonyl-hexyl)-5,6,7,7a-tetrahydroindan-5-one as a colorless oil.

IR bands at 5.78 $\mu$ and 6.05 $\mu$.

b. 6.4 g. of racemic 1$\beta$-trimethylacetoxy-7a$\beta$-methyl-4-(3'-keto-6'-metoxy-carbonyl-hexyl)-5,6,7,7a-tetrahydroindan-5-one is dissolved in 50 ml. of toluene and 10 ml. of 2,2-dimethoxypropane, cooled to 0° C., and mixed with 3 mg. of p-toluenesulfonic acid. After a reaction time of 16 hours at 0° C., the mixture is worked up as usual, the crude product is recrystallized from ether, and 6.1 g. of 1$\beta$-trimethylacetoxy-7a$\beta$-methyl-4-(3',3'-dimethoxy-6'-methoxycarbonyl-hexyl)-5,6,7,7a-tetrahydroindan-5-one is thus obtained, m.p. 101°–103° C.

c. 5.9 g. of racemic 1$\beta$-trimethylacetoxy-7a$\beta$-methyl-4-(3', 3'-dimethoxy-6'-methoxycarbonyl-hexyl)-5,6,7,7a-tetrahydroindian-5-one is reacted as described in Example 1(g), worked up, and the product is 5.31 g. of 3-methoxy-7$\alpha$-trimethylacetoxy-6a$\alpha$-methyl-3-(3'-methoxycarbonyl-propyl)-1,2,3,5,6,6a,7$\beta$,8-octahydrocyclopenta-[f][1]-benzopyran as a colorless oil.

IR bands at 5.77 $\mu$ and 6.05 $\mu$.

d. 1.83 g. of racemic 3-methoxy-7$\alpha$-trimethylacetoxy-6a$\alpha$-methyl-3-(3'-methoxycarbonyl-propyl)-1,2,3,5,6,6a,7$\beta$,8-octahydrocyclopenta-[f][1]-benzopyran is hydrogenated as described in Example 1(h), then worked up, and the product is 1.65 g. of 3-methoxy-7$\alpha$-trimethylacetoxy-6a$\alpha$-methyl-3-(3'-methoxycarbonylpropyl)-1,2,3,5,6,6a,7$\beta$,8,9,9a$\beta$-decahydrocyclopenta-[f][1]-benzopyran as a colorless oil.

IR bands at 5.78 $\mu$.

EXAMPLE 5 a. 23 g. of 1$\beta$-tert.-butyloxy-7a$\beta$-methyl-5,6,7,7a-tetrahydroindan-5-one is refluxed for 5 hours in 250 ml. of absolute tetrahydrofuran with 2.5 g. of sodium hydride under an argon atmosphere.

Then, the reaction mixture is cooled to −30° C., and within one hour 22 g. of ethyl 7-chloro-5-ketoheptanoate in 100 ml. of absolute tetrahydrofuran is added dropwise thereto. The mixture is allowed to stand at −30° C. for 2 hours and then allowed to reach room temperature during the course of 16 hours. The mixture is worked up as described in Example 1(e), thus producing 20.4 g. of 1$\beta$-tert.-butyloxy-7a$\beta$-methyl-4-(3'-keto-6'-ethoxycarbonyl-hexyl)-5,6,7,7a-tetrahydroindan-5-one as a colorless oil. $[\alpha]_D^{21} = +49°$ ($c = 1$, benzene).

b. 5 g. of 1$\beta$-tert.-butyloxy-7a$\beta$-methyl-4-(3'-keto-6'-ethoxycarbonyl-hexyl)-5,6,7,7a-tetrahydroindan-5-one is reacted according to Example 1(f) with methanol and trimethyl orthoformate and catalytic amounts of p-toluenesulfonic acid at 0° C.; then, the mixture is worked up, thus obtaining 1$\beta$-tert.-butyloxy-7a$\beta$-methyl-4-(3', 3'-dimethoxy-6'-ethoxycarbonyl-hexyl)-5,6,7,7a-tetrahydroindan-5-one as a colorless oil.

IR bands at 5.76 $\mu$ and 6.04 $\mu$. $[\alpha]_D^{21} = +44°$ ($c = 1$, benzene).

c. 4.6 g. of 1$\beta$-tert.-butyloxy-7a$\beta$-methyl-4-(3',3'-dimethoxy-6'-ethoxycarbonyl-hexyl)-5,6,7,7a-tetrahydroindan-5-one is dissolved in 100 ml. of benzene and refluxed with 100 mg. of malonic acid as set forth in Example 1(g). The mixture is then worked up, thus producing 4.22 g. of 3-methoxy-7α-tert.butyloxy-6aα-methyl-3-(3'-ethoxycarbonylpropyl)-1,2,3,5,6,6a,7β,8-octahydrocyclopenta-[f][1]-benzopyran.

IR bands at 5.75 μ and 6.02 μ.
$[\alpha]_D^{21} = +2.6°$ ($c = +1$, benzene).

d. 5.9 g. of 3-methoxy-7α-tert.-butyloxy-6aα-methyl-3-(3'-ethoxycarbonylpropyl)-1,2,3,5,6,6a,7β,8-octahydrocyclopenta-[f][1]-benzopyran is hydrogenated analogously to Example 1(h). After chromatographical purification on a silica gel column, one obtains 5.35 g. of 3-methoxy-7α-tert.butyloxy-6aα-methyl-3-(3'-ethoxycarbonylpropyl)-1,2,3,5,6,6a,7β,8,9-,9aβ-decahydrocyclopenta-[f][1]-benzopyran.

IR bands at 5.76 μ.
$[\alpha]_D^{21} = +18.9°$ ($c = 1$, benzene).

EXAMPLE 6 a. 132 g. 5-oxohexanonitrile is dissolved in 700 ml. of benzene; 150 g. of 2,2-dimethylpropanediol and 2 g. of p-toluenesulfonic acid are added thereto, and the mixture is heated for 24 hours on a water trap. Then, the mixture is allowed to cool, mixed with 150 ml. of saturated sodium bicarbonate solution, and worked up as usual. The thus-obtained crude product is purified by high vacuum distillation, resulting in 207 g. of 5,5-(2',2'-dimethylpropylenedioxy)-hexanonitrile, B.p. 0.1 torr. = 93–94° C.

b. 75 g. of 5,5-(2',2'-dimethylpropylenedioxy)-hexanonitrile is dissolved in 750 ml. of absolute toluene; the solution is cooled to −50° C. and mixed dropwise with 315 ml. of a 20% diisobutyl aluminum hydride solution in toluene. the mixture is stirred for one hour at −50° C., and within 10 minutes 500 ml. of saturated sodium dihydrogen phosphate solution is added thereto. The mixture is agitated for another 5 hours at room temperature and then worked up as usual. The resultant crude product is purified by way of an aluminum oxide column, thus producing 57.3 g. of 5,5-(2',2'-dimethylpropylenedioxy)-hexanal as a colorless oil.

IR bands at 5.8 μ.

c. 23 g. of 5,5-(2',2'-dimethylpropylenedioxy)-hexanal is reacted with vinyl magnesium chloride as described in the first paragraph of Example 1(c). Then, the thus-produced crude substance is dissolved in 500 ml. of absolute methylene chloride, the solution is mixed with 200 mg. of hydroquinone and 300 g. of active pyrolusite, and the mixture is shaken for 8 hours. Then, the mixture is filtered, the solution is concentrated under vacuum, the resultant crude product is purified by chromatography over a silica gel column, and the final product is 17.3 g. of 7,7-(2',2'-dimethylpropylenedioxy)-1-octen-3-one as a colorless oil.

IR bands at 5.97 μ.

d. 5. g. of 1β-tert.butyloxy-7aβ-methyl-5,6,7,7a-tetrahydroindan-5-one is dissolved in 50 ml. of absolute dimethoxyethane and mixed with a solution of 100 mg. of sodium in 5 ml. isopropanol. After this solution has been added, 15 minutes are allowed to elapse, and then a solution of 5.8 g. of 7,7-(2',2'-dimethylpropylenedioxy)-1-octen-3-one in 20 ml. of absolute dimethoxyethane is added dropwise within 60 minutes. Thereafter, the mixture is agitated for 40 hours at room temperature. After the addition of 10 ml. of saturated primary sodium hydrogen phosphate solution, the mixture is worked up as set forth in Example 1(f), and the crude product is purified by chromatography on silica gel by means of hexane-acetone gradients, thus obtaining 3.75 g. of 1β-tert.butyloxy-7aβ-methyl-4-[7',7'-(2'',2''-dimethylpropylenedioxy)-3'-ketooctyl]-5,6,7,7a-tetrahydroindan-5-one.

IR bands at 5.86 μ and 6.03 μ.
$[\alpha]_D^{20} = +47.5°$($c = 1$, benzene).

e. 7.8 g. of 1β-tert.-butyloxy-7aβ-methyl-4-[7',7'-(2'',2''-dimethylpropylenedioxy)-3'-ketooctyl]-5,6,7,7a-tetrahydroindan-5-one is dissolved in 80 ml. of absolute ethanol and 10 ml. of triethyl orthoformate. Then, the mixture is cooled to 0° C., and 5 mg. of p-nitrophenol is added thereto. After a reaction time of 7 hours at 0° C., the mixture is poured into 500 ml. of dilute sodium bicarbonate solution and worked up as usual, thus producing 7.95 g. of 1β-tert.-butyloxy-7aβ-methyl-4-[3',3'-diethoxy-7',7'-(2'',2''-dimethylpropylenedioxy)-octyl]-5,6,7,7a-tetrahydroindan-5-one as a colorless oil.

IR band at 6.05 μ.
$[\alpha]_D^{21} = +42°$ ($c = 1$, benzene).

f. 1.9 g. of 1β-tert.-butyloxy-7aβ-methyl-4-[3',3'-diethoxy-7',7'-(2'',2''-dimethylpropylenedioxy)-octyl]-5,6,7,7a-tetrahydroindan-5-one is reacted, in accordance with Example 1(g), with 50 mg. of 2,4-dinitrophenol in benzene, then worked up as usual, and the product thus obtained is 1.62 g. of 3-ethoxy-7β-tert.butyloxy-6aα-methyl-3-[4'-(2'',2''-dimethylpropylenedioxy)-pentyl]-1,2,3,5,6,6a,7β,8-octahydrocyclopenta-[f][1]-benzopyran as a colorless oil.

IR band at 6.02 μ.
$[\alpha]_D^{21} = +2.1°$ ($c = 1$, benzene).

g. 1.35 g. of 3-ethoxy-7α-tert.-butyloxy-6aα-methyl-3-[4'-(2'',2''-dimethylpropylenedioxy-pentyl]-1,2,3,5,6,6a,7β,8-octahydrocyclopenta-[f][1]benzopyran is hydrogenated analogously to Example 1(h). The crude product of this hydrogenation is purified by chromatography on aluminum oxide, resulting in 0.98 g. of 3-ethoxy-7α-tert.butyloxy-6a,α-methyl-3-[4'-(2'',2''-dimethylpropylenedioxy)-pentyl]-1,2,3,5,6,6a,7,β,8,9-,9aβ-decahydrocyclopenta-[f][1]-benzopyran as a colorless oil.

$[\alpha]_D^{21} = +17.5°$ ($c = 1$, benzene).

EXAMPLE 7 a. 33.5 g. of racemic 7 a-methyl-5,6,7,7a-tetrahydroindan-1,5-dione is dissolved in 450 ml. of absolute dimethoxyethane; the solution is mixed with 5.1 g. of sodium hydride and agitated at 50°–55° C. for 5 hours under an argon atmosphere. Then, the mixture is cooled to -10° C, and within 30 minutes a solution of 57 g. of 7,7-o-phenylenedioxy-1-chloroctan-3-one in 300 ml. of absolute dimethoxyethane is added dropwise; then, the mixture is agitated for 6 hours at 0° C. The reaction mixture is thereafter mixed with 100 ml. of sodium dihydrogen phosphate solution and worked up. The thus-obtained crude product is purified over a silica gel column with a hexane-acetone gradient, resulting in 34.95 g. of rac.-7a-methyl-4-(7',7'-o-phenylenedioxy-3'-ketoocytyl)-5,6,7,7a-tetrahydroindan-1,5-dione in the form of a light yellow oil.

IR bands at 5.73 μ; 5.86 μ; 6.07 μ; 6.73 μ; and 8.1 μ.

b. 32.1 g. of rac.-7a-methyl-4-(7',7'-o-phenylenedioxy-3'-ketooctyl)-5,6,7,7a-tetrahydroindan-1,5-dione is dissolved in 300 ml. of methanol and 32.1 ml. of orthoformic acid ester; the solution is cooled to 0° C., mixed with 4 ml. of a 5% methanolic p-toluenesulfonic acid solution, and stored for 4 hours at 0° C. Then, the reaction mixture is poured into 1 l. of ice-cold sodium bicarbonate solution, extracted with methylene chloride, the methylene chloride phase is washed with 15% sodium chloride solution, dried over sodium sulfate, and concentrated under vacuum, thus obtaining 31.2 g. of rac.-7-a-methyl-4-(3',3'-dimethoxy-7',7'-o-phenylenedioxyoctyl)-5,6,7,7a-tetrahydroindan-1,5-dione as a yellow oil.

IR bands at 5.74 μ; 6.07 μ; 6.73 μ; and 8.09 μ.

c. 31.2 g. of rac.-7a-methyl-4-(3',3'-dimethoxy-7',7'-o-phenylenedioxyoctyl)-5,6,7,7a-tetrahydroindan-1,5-dione is dissolved in 600 ml. of absolute benzene, mixed with 200 mg. of malonic acid, and heated to the boiling point for 90 minutes, withdrawing 300 ml. of distillate. The cooled solution is then mixed with 100 ml. of sodium bicarbonate solution and the mixture is worked up. The thus-obtained crude product is purified over a silica gel column, resulting in 29.3 g. of rac.-3-methoxy-6a-methoxy-3-(4',4'-o-phenylenedioxypentyl)-2,3,5,6,6a,8-hexahydrocyclopenta-[f][1]-benzopyran-7[1H]-one.

IR bands at 5.75 μ; 6.01 μ; 6.75 μ; and 8.1 μ.

d. 25.6 g. of rac.-3-methoxy-6a-methyl-3-(4',4'-o-phenylenedioxypentyl)-2,3,5,6,6a,8-hexahydrocyclopenta-[f][1]-benzopyran-7[1H]-one is dissolved in 250 ml. of absolute tetrahydrofuran, then added dropwise within 20 minutes to an ice-cold suspension of 1.5 g. of lithium aluminum hydride in 100 ml. of absolute tetrahydrofuran in such a manner that the reaction temperature does not exceed 10° C. The reaction mixture is allowed to stand for 60 minutes udner ice cooling, and then 1.5 ml. of water, 1.5 ml. of 15% aqueous sodium hydroxide solution, and again 4.5 ml. of water are added dropwise to the solution. The solids are filtered off and washed twice with respectively 50 ml. of absolute ether. The combined solutions are concentrated under vacuum, thus obtaining 24.7 g. of rac.-3-methoxy-6aα-methyl-3-(4',4'-o-phenylenedioxypentyl)-2,3,5,6,6a,8-hexahydrocyclopenta-[f][1]-benzopyran-7[1H]α-ol as an almost colorless oil.

IR bands at 6.1 μ; 6.73 μ; and 8.09 μ.

e. 23.1 g. of rac.-3-methoxy-6aα-methyl-3-(4',4'-o-phenylenedioxypentyl)-2,3,5,6,6a,8-hexahydrocyclopenta-[f][1]-benzopyran-7[1H]α-ol is dissolved in 400 ml. of ethyl acetate, mixed with 3 g. of palladium charcoal, and hydrogenated at room temperature with hydrogen under normal pressure until somewhat more than the theoreticaly required amount is absorbed. Then, the catalyst is filtered off, the solution is concentrated under vacuum, the residue is purified by chromatography over a silica gel column, and the resultant product is 19.7 g. of rac.3-methoxy-6aα-methyl-3-(4',-4'-o-phenylenedioxypenyl)-2,3,5,6,6a,8,9,9aβ-octahydrocyclopenta-[f][1]-benzopyran-7[1H]α-ol as a colorless oil.

IR bands at 6.73 μ and 8.1 μ.

The preceding examples can be repeated with similar success by substituting the generally and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzopyran of the formula

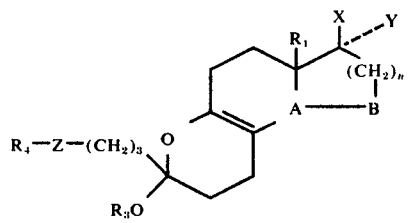

wherein -A-B- is >CH-CH$_2$— or >CH=CH-; $n$ is the integer 1 or 2; $R_1$ $R_3$ each are lower alkyl; X is hydroxy, acyloxy wherein acyl is the acyl radical of a hydrocarbon carboxylic acid of 1–10 carbon atoms optionally substituted by phenyl or alkoxy of 1–10 carbon atoms optionally substituted by phenyl; Y is H or X and Y collectively are oxo; Z is arylene dioxy methylene; and $R_4$ is lower alkyl.

2. A compound according to claim 1, wherein $R_4$ is methyl or ethyl.

3. A benzopyran according to claim 1 wherein $n$ is 1.

4. A benzopyran according to claim 1 wherein $R_1$ $R_3$ are each methyl or ethyl.

5. A benzopyran according to claim 1 wherein >A-B- is >C=CH-.

6. A benzopyran according to claim 1 wherein >A-B- is >CH-CH$_2$.

7. A benzopyran according to claim 1 wherein X is hydroxy.

8. A benzopyran according to claim 1 wherein X is esterified or etherified hydroxyl.

9. A benzopyran according to claim 1 wherein $n$ is 1, $R_1$ and $R_3$ are each methyl or ethyl and X is hydroxyl.

10. A compound according to claim 1, 3-methoxy-6aα-methyl-3-(4',4',-o-phenylenedioxypentyl)-2,3,5,6,6a,8-hexahydrocyclopenta-[f][1]-benzopyran-7[1H]-one.

11. A compound according to claim 1, 3-methoxy-6aα-methyl-3-(4',4'-o-phenylenedioxypentyl)-2,3,5,6,6a, 8hexahydrocyclopenta[f][1]-benzopyran-7[1H]α-ol.

12. A compound according to claim 1, 3-methoxy-7βtert.-butyloxy-6aα-methyl-3-(4',4'-o-phenylenedioxypentyl)-1,2,3,5,6,6a,7β,8,9,9aβ-decahydrocyclopenta-[f][1]-benzopyran.

13. A compound according to claim 1, 3-methoxy-7a-tert.-butyloxy-6aα-ethyl-3-(4',4'-o-phenylenedioxypentyl)-1,2,3,5,6,6a,7β,8-octahydrocyclopenta[f][1]-benzopyran.

14. A compound according to claim 1, 3-methoxy-7α-tert.-butyloxy-6aα-ethyl-3-(4',4'-o-phenylenedioxypentyl)-1,2,3,5,6,6a,7β,8,9,9aβ-decahydrocyclopenta-[f][ ]-benzopyran.

* * * * *

UNITED STATES PATENT AND TRADEMARK OFFICE
CERTIFICATE OF CORRECTION

PATENT NO. : 4,032,540
DATED : June 28, 1977
INVENTOR(S) : Ulrich Eder, et al

It is certified that error appears in the above-identified patent and that said Letters Patent are hereby corrected as shown below:

Claim 1, Column 16, line 20: after "$R_1$" insert -- and --.

Claim 4, Column 16, line 30: after "$R_1$" insert -- and --.

Claim 14, Column 16, line 61: after "[f]" cancel "[ ]" and insert in its place -- [1] --.

Signed and Sealed this

*Twenty-seventh* Day of *September 1977*

[SEAL]

*Attest:*

RUTH C. MASON
*Attesting Officer*

LUTRELLE F. PARKER
*Acting Commissioner of Patents and Trademarks*